US00PP11077P

United States Patent [19]

Yu-Lin

[11] Patent Number: Plant 11,077

[45] Date of Patent: Oct. 5, 1999

[54] APPLE TREE NAMES 'HUAGUAN'

[75] Inventor: Wang Yu-Lin, Auckland, New Zealand

[73] Assignee: Fruit Industry Plant Improvement Agency, Hastings, New Zealand

[21] Appl. No.: 08/982,985

[22] Filed: Dec. 2, 1997

[51] Int. Cl.[6] ..... A01H 5/00

[52] U.S. Cl. ..... Plt./161

[58] Field of Search ..... Plt./34.1, 161

[56] References Cited

PUBLICATIONS

UPOV CD–ROM, Apple tree named 'Huaguan', PBR APP123, New Zealand, 1996.

UPOV CD–ROM, Apple tree named 'Huaguan', PBR 96–972, Canada, 1996.

UPOV CD–ROM, Apple tree named 'Huaguan', 96272, Australlia, 1996.

UPOV CD–ROM, Apple tree named 'Huauan', PBR 9275, Japan, 1996.

*Primary Examiner*—Howard J. Locker

*Assistant Examiner*—Melissa L. Kimball

*Attorney, Agent, or Firm*—Klarquist Sparkman Campbell Leigh & Whinston, LLP

[57] ABSTRACT

A new and distinct variety of apple tree named 'Huaguan' characterized by: (1) a semi-spur tree with medium vigor that blooms in mid-season, produces many fruiting spurs, and has spreading branches due to early and heavy fruit production; (2) deep red buds opening to a blossom having white petals tinged with a light pink; (3) fruit having a variable conical to ovate shape, a short to medium stem, a deeper calyx bowl than 'Fuji', a creamy yellow flesh, a sweet, slightly tart flavor and distinguishing aroma, an attractive yellowish green to golden yellow skin color overlaid with a very attractive striped blush made up of fine bright crimson red stripes; and (4) dark green leaves with sinuate, serrate margins, prominent veins on the bottom side, and an underside covered with a medium buff/green pubescence.

4 Drawing Sheets

BACKGROUND OF THE INVENTION

The present invention comprises a new and distinct variety of apple tree, referred to by the varietal name Huaguan. The English translation of the varietal name Huaguan is 'Chinese Champion'.

The original tree of the new variety was discovered in 1989 in a cultivated area in Zhengzhou, Henan province, People's Republic of China. 'Huaguan' is a selection from a controlled cross of 'Golden Delicious'×'Fuji'. Throughout this description, 'Golden Delicious' refers to the unpatented standard 'Golden Delicious' variety of apple tree and 'Fuji' refers to the unpatented standard 'Fuji' variety of apple tree.

Trees of 'Huaguan' were observed at the Washington State University Research Station at Prosser, Wash., and in test plots of the Pacific Northwest Fruit Tester's Association in Selah, Wash., and were compared to 'Fuji' trees of similar age.

This invention has not been observed under all possible environmental conditions. However, the following combination of traits have been repeatedly observed in asexually propagated progeny and are determined to be the basic characteristics of this invention, which in combination distinguish 'Huaguan' as a new and distinct variety: (1) a semi-spur tree with medium vigor that blooms in mid-season, produces many fruiting spurs, and has spreading branches due to early and heavy fruit production; (2) deep red buds opening to a blossom having white petals tinged with a light pink; (3) fruit having a variable conical to ovate shape, a short to medium stem, a deeper calyx bowl than 'Fuji' apples, a creamy yellow flesh, a sweet, slightly tart flavor and distinguishing aroma, an attractive yellowish green to golden yellow skin color overlaid with a very attractive striped blush made up of fine bright crimson red stripes; and (4) dark geeen leaves with sinuate, serrate margins, prominent veins on the bottom side, and an underside covered with a medium buff/green pubescence Asexual reproduction by budding at Prosser, Wash. and elsewhere shows that these characteristics are established and transmitted through succeeding asexual propagations.

BRIEF DESCRIPTION OF THE PHOTOGRAPHS

DETAILED DESCRIPTION

Figure 1:
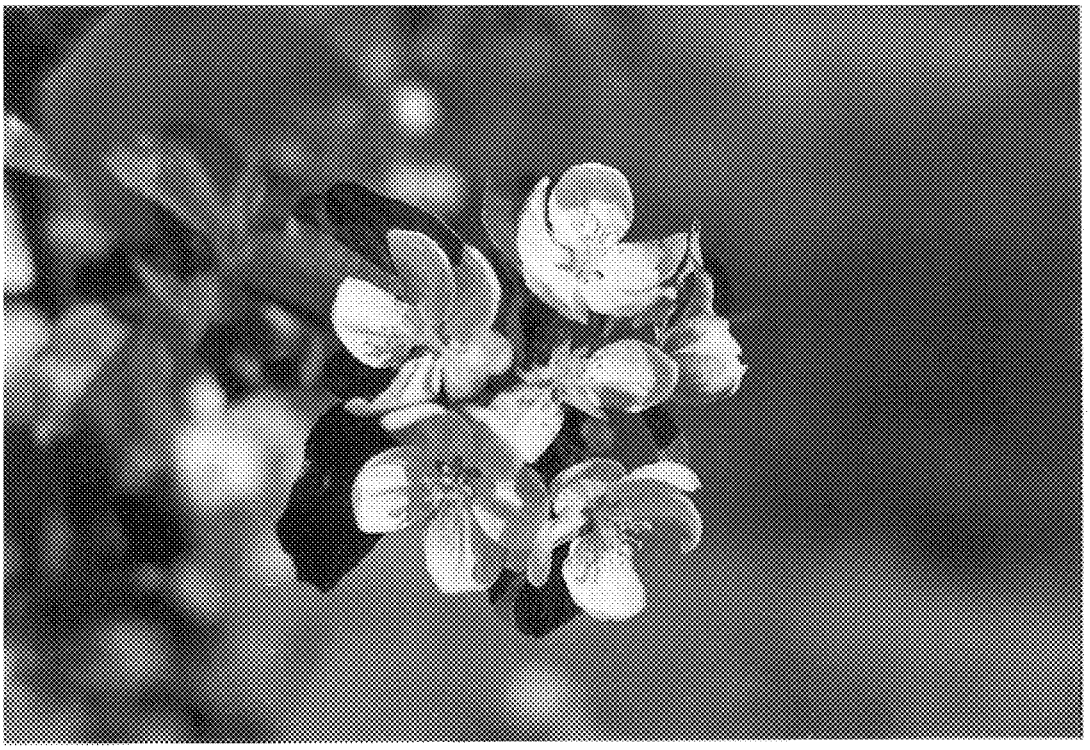
FIG. 1 is a view of blossoms of 'Huaguan'.
Figure 2:
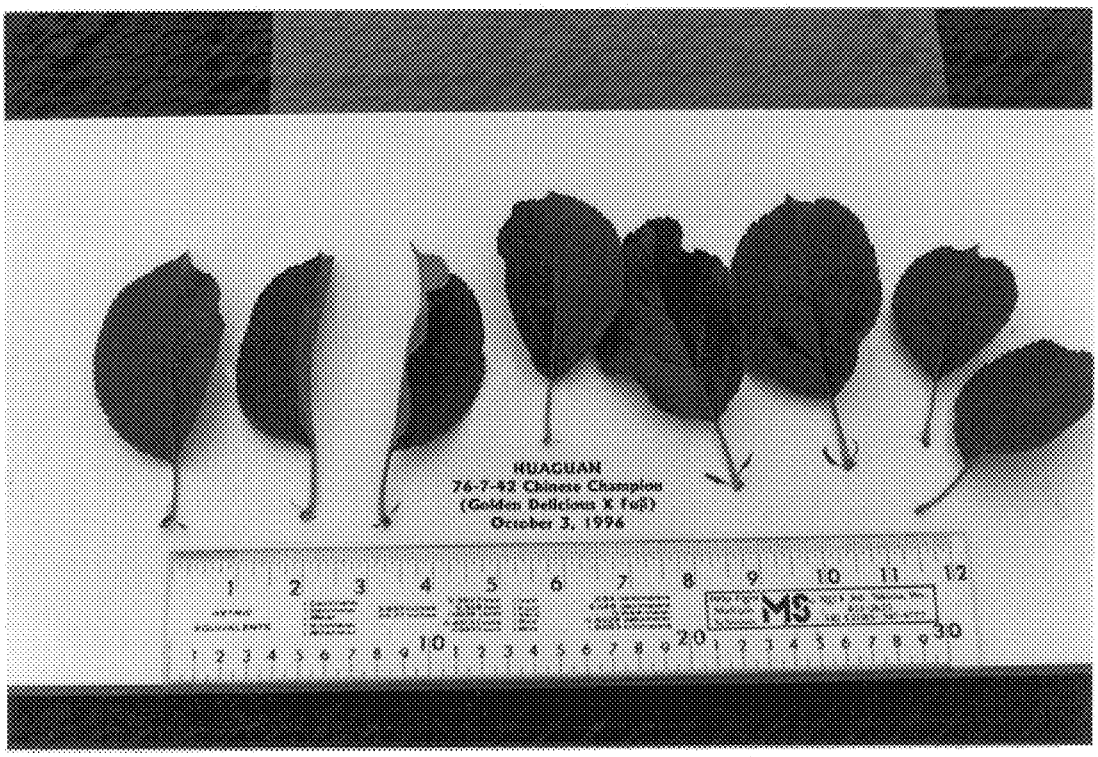
FIG. 2 is a view of leaves of 'Huaguan'.
Figure 3:
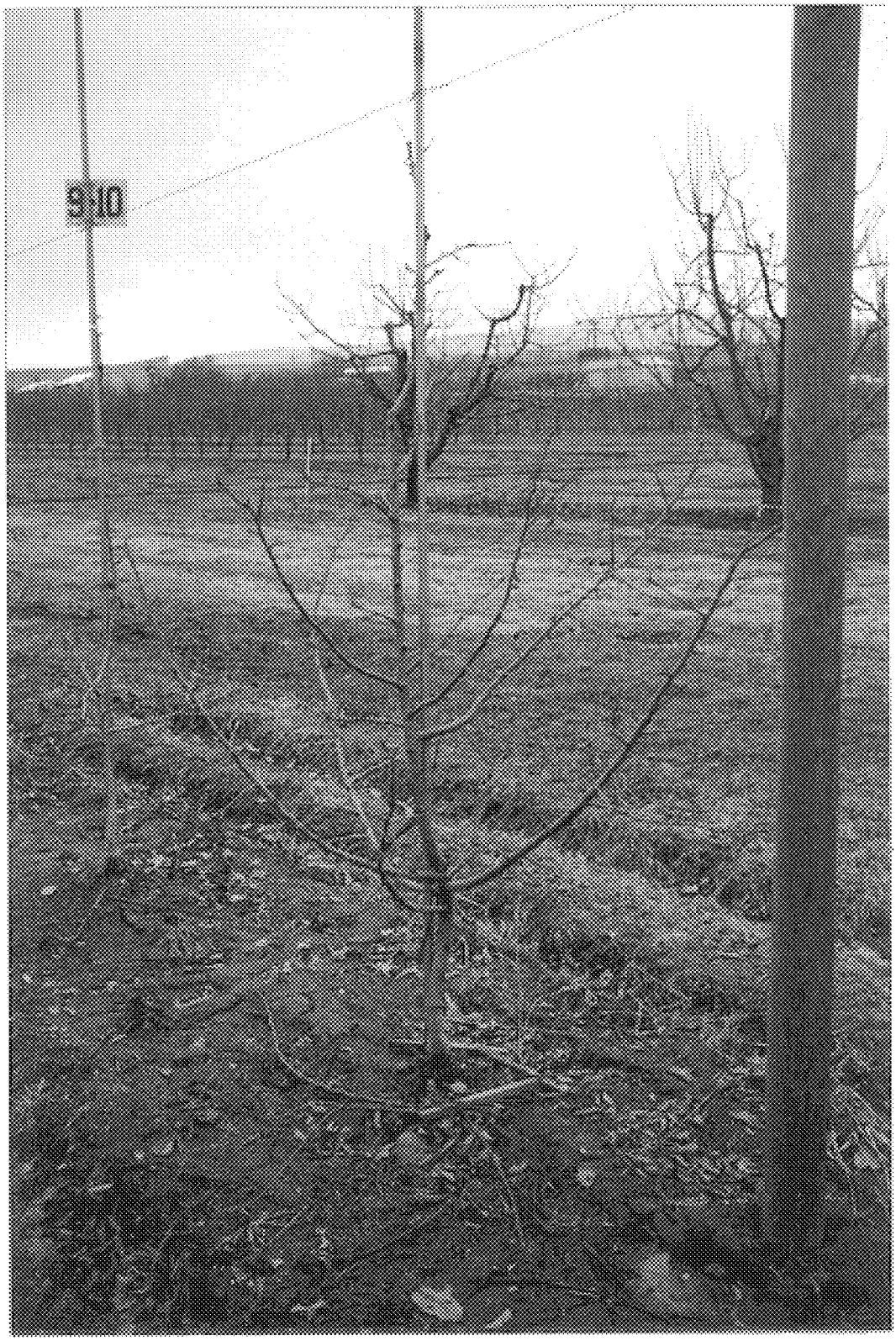
FIG. 3 is a view of a tree of 'Huaguan' that was planted in 1992 (photograph taken in Feb. 1997).
Figure 4:
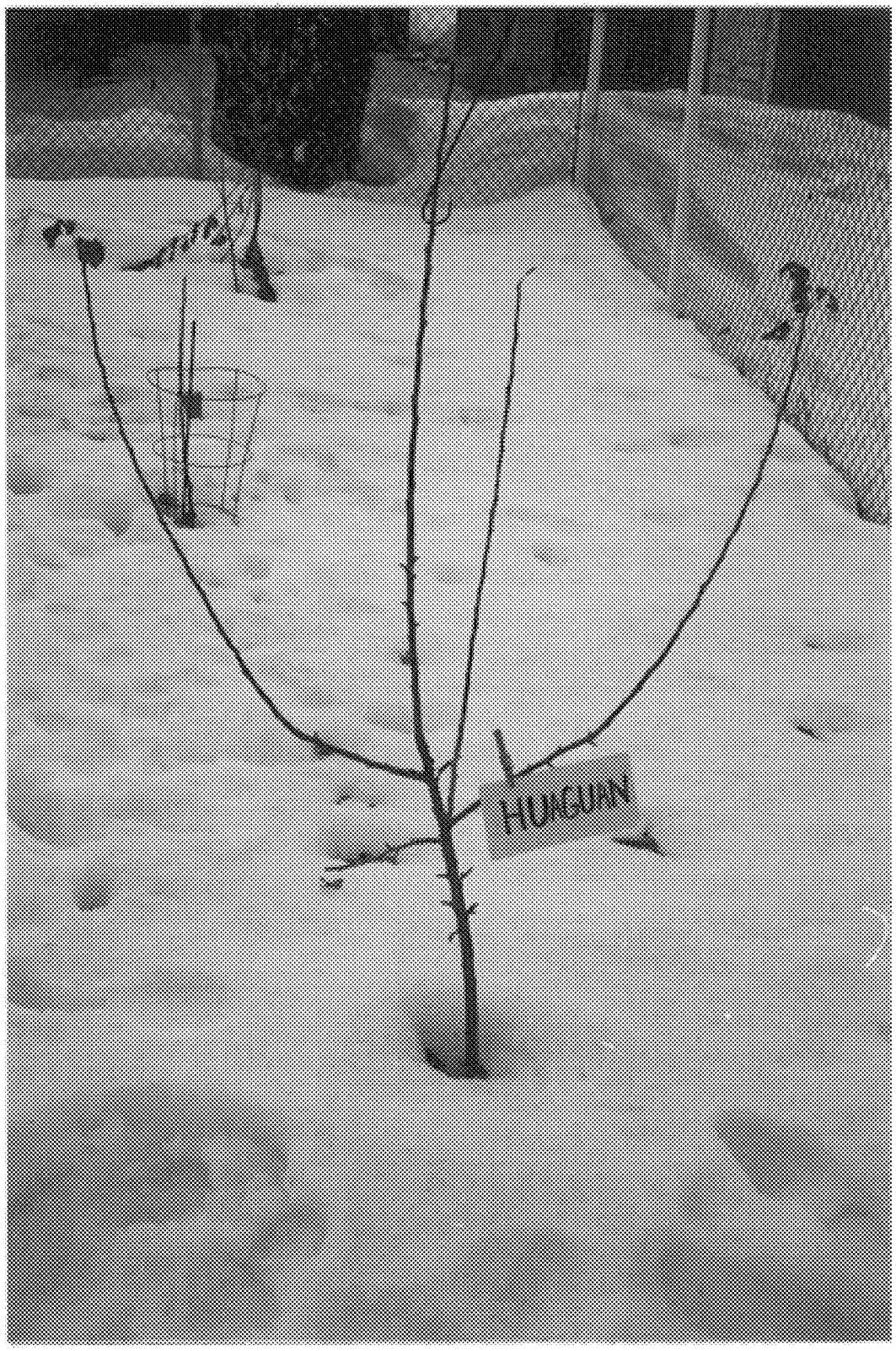
FIG. 4 is a view of a two-year-old tree of 'Huaguan' showing the many precocious fruiting spurs which lead to early production.
Figure 5:
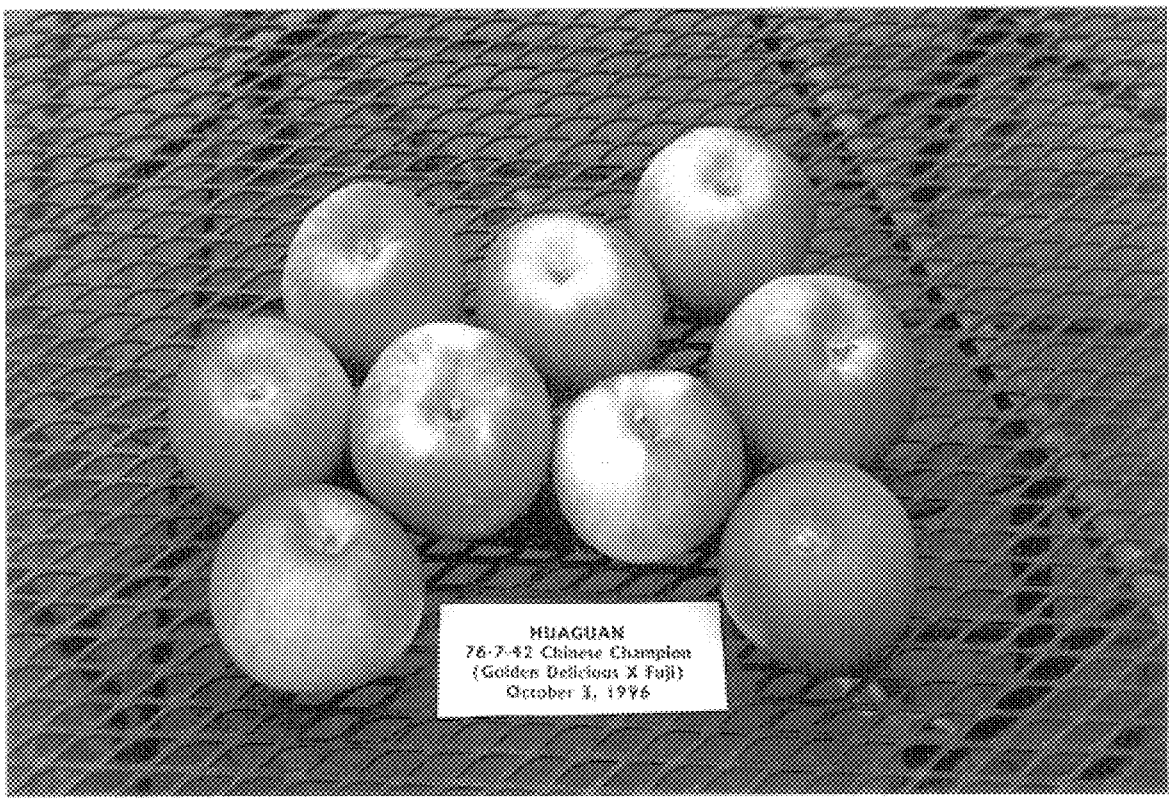
FIG. 5 shows stem end and calyx end views of fruit of 'Huaguan'.

The following is a detailed description of the invention based on trees of the Huaguan variety grown under orchard practices at the Washington State University research plot at Prosser, Wash., in a test plot near Proser, Wash., and at a test plot in Selah, Wash. Observations were made from 1994 through 1996. All trees were bearing on the dwarfing 'Malling 26' (unpatented variety) rootstock.

Color references employ terms of ordinary dictionary significance, except where reference is made to The Royal Horticultural Colour Chart (R.H.S.). It should be noted colors do vary depending upon factors such as growing and lighting conditions.

All trees of the new variety, insofar as I have been able to observe them, are identical in all the characteristics described below.

Species: *Malus pumila.*

Parentage: 'Golden Delicious'×'Fuji'.

Propagation: Holds to distinguishing characteristics through succeeding propagation by budding.

Dates of first and last picking: Varies with growing season. In 1996, fruit was picked from September 8–14.

Tree:

*Vigor.*—Medium (less than 'Fuji' or 'Golden Delicious') with early and heavy bearing.

*Habit.*—Standard tree type with spreading branches due to early and heavy production of fruit.

*Lenticels.*—Small, inconspicuous, color light buff to yellow.

Leaves:

*Size.*—3.5 to 4.0 cm wide, 6.0 to 7.0 cm long.

*Shape.*—Ovate to oblong with sinuate, serrate margins.

*Color.*—Upper side: Dark green (like R.H.S. 139A) with prominent veins. Underside: Like R.H.S. 139A but lighter than the upper leaf surface Covered with a medium buff/green pubescence.

*Margin.*—Fine to medium serrations.

*Petiole.*—2.0 to 3.0 cm. Color variable, typically green.

*Flower.*—Tight, dark red buds (somewhat like R.H.S. 63A) open to a blossom with white petals (whiter than R.H.S. 155D) tinged with a slight pink blush, similar to 'Golden Delicious'. Blooms midseason (same as 'Fuji', 2–3 days before 'Huashuai' (U.S. Plant patent application Ser. No. 08/982,984) over a period of eight to fourteen days in most years. Although variable with weather conditions, in Selah, Wash. during 1997, the first blooms of the 'Huaguan' variety were observed on April $28^{th}$ and peak bloom was observed May $2^{nd}$–$5^{th}$. The bloom has five carpels typically of apple trees and usual ovaries. Insofar, as observed, the pollen, styles and other reproductive organs are like, 'Fuji'.

Fruit:

*Size.*—Variable, typical 3.5 to 4.0 cm diameter.

*Shape.*—Varies from round to ovate to conical, and, depending on seed count, may become slightly lop-sided.

*Stem cavity.*—Deep (1.5 cm).

*Basin cavity.*—Deep (1.5 cm) and generally smooth, without the five points found on varieties such as 'Bisbee' (U.S. Plant Pat. No. 1,564 for the 'Bisbee' red delicious apple tree).

*Stem.*—Medium slender. Length short (1.5 cm) to medium (2.5 cm), generally shorter than 'Fuji' (up to 3.5+ cm).

*Calyx.*—Inconspicuous, generally tightly closed.

*Carpels.*—Five, tightly clustered.

*Skin.*—Smooth. Good wax layer that can produce a bright shine. Not russet prone.

*Ground color.*—Greenish yellow to golden yellow from first to last picking (like R.H.S. 145B although yellows with maturity).

*Color markings/overcolor.*—Very attractive pink to red blush made up of fine bright crimson red stripes (like R.H.S. 53B).

*Lenticels.*—Numerous, very inconspicuous.

*Color of lenticels.*—Buff to yellow.

*Flesh.*—Fine, crisp and very juicy. Color: Creamy yellow (compared to the creamy white of 'Fuji'). Flavor: Rated high, sweet, slightly tart (less acidity than 'Fuji'), with distinguishing aroma.

*Quality.*—Very good. Rated better than 'Fuji' in China because of long storage and shelf life and market acceptance.

*Core.*—Bundle area is 2 cm wide and up to 6 cm long. Bundles: Five. Core lines: Well defined. Calyx-tube: Short and tightly closed. Cell walls: Thinner than 'Fuji'.

*Seeds.*—Number per cell: Maximum of four, usually fewer in a poor pollination year. Length: 0.5 to 0.75 cm. Breadth: 0.25 cm. Color: Black.

*Use.*—A superior fresh-eating cultivar, excellent for pies, sauce and juice.

*Keeping quality.*—Very good. Fruit remains firm and crisp at room temperature for a week.

*Storage.*—Up to six months in common storage and full year in CA.

Production: Moderate, similar to both parents.

Pollination: Requires pollination by another diploid variety that blooms in mid-season such as 'Huashuai', 'Bisbee' and 'Fuji'.

Resistance to insects and disease: Mildly susceptible to mildew and fireblight. Very susceptible to scab. Vulnerable to all insect pests of apple.

I claim:

1. A new and distinct variety of apple tree substantially as herein shown and described.

* * * * *